(12) United States Patent
Rajadhyaksha et al.

(10) Patent No.: US 6,703,208 B1
(45) Date of Patent: Mar. 9, 2004

(54) IMMUNOLOGICAL ASSAY FOR DETECTION OF ANTIBODIES IN CELIAC DISEASE

(75) Inventors: Manoj Rajadhyaksha, Williamsville, NY (US); Vijay Kumar, Williamsville, NY (US)

(73) Assignee: Immco Diagnostics, Buffalo, NY (US)

( * ) Notice: Subject to any disclaimer, the term of this patent is extended or adjusted under 35 U.S.C. 154(b) by 428 days.

(21) Appl. No.: 09/690,637

(22) Filed: Oct. 17, 2000

Related U.S. Application Data

(60) Provisional application No. 60/160,548, filed on Oct. 20, 1999.

(51) Int. Cl.[7] .............................................. G01N 35/53
(52) U.S. Cl. ..................... 435/7.2; 435/7.4; 435/7.5; 435/7.92; 435/21; 435/40.5; 436/63; 436/86; 436/151; 424/130.1; 424/134.1
(58) Field of Search ..................... 435/7.2, 7.4, 7.5, 435/7.92, 21, 40.5, 345; 436/63, 86, 151; 424/130.1, 134.1

(56) References Cited

U.S. PATENT DOCUMENTS

| | | | |
|---|---|---|---|
| 5,716,794 A | 2/1998 | Tjota | 435/7.92 |
| 5,817,523 A | 10/1998 | Picarelli | 436/503 |
| 5,972,615 A | 10/1999 | An et al. | |

FOREIGN PATENT DOCUMENTS

| | | | | |
|---|---|---|---|---|
| WO | WO 91/17444 | 11/1991 | | |
| WO | WO 92/10761 | * 6/1992 | .......... | G01N/33/86 |
| WO | 9710508 | 3/1997 | | |
| WO | 9803872 | 1/1998 | | |
| WO | WO 99/05918 | * 2/1999 | .......... | A23J/3/34 |
| WO | WO 00/24773 | 5/2000 | | |

OTHER PUBLICATIONS

Dieterich, et al, Identification of Tissue Transglutaminase as the Autoantigen of Celiac Disease, Nat. Med. 1997 Jul; 3(7):797–801.

Maki, Tissue Transglutaminase as the Autoantigen of Coeliac Disease, Gut 1997 Oct;41(4):565–6.

Schuppan, et al., Identification of the Autoantigen of Celiac Disease, Annals of the New York Academy of Sciences, 1998, vol. 859, pp. 121–126.

Dieterich, et al., Autoantibodies to Tissue Transglutaminase as Predictors of Celiac Disease. Gastroenterology 1998, vol. 115, No. 6, pp. 1317–1321.

Sollid, et al., New Tool to Predict Celiac Disease on its Way to the Clinics. Gastroenterology 1998, vol. 115, No. 6, pp. 1584–1586.

* cited by examiner

Primary Examiner—Long V. Le
Assistant Examiner—Changhwa J Cheu
(74) Attorney, Agent, or Firm—Hodgson Russ LLP

(57) ABSTRACT

The present invention discloses a method for the detection of antibodies in celiac disease. The method comprises detecting antibodies in serum, to a combination of transglutaminase and a substrate therefor.

12 Claims, No Drawings

IMMUNOLOGICAL ASSAY FOR DETECTION OF ANTIBODIES IN CELIAC DISEASE

This application claims the priority of U.S. provisional application No. 60/160,548 filed on Oct. 20, 1999, the disclosure of which is incorporated herein by reference.

BACKGROUND OF THE INVENTION

1. Field of the Invention

The present invention relates generally to the field of celiac disease. More particularly, the present invention provides a sensitive immunological assay for the detection of antibodies implicated in celiac disease.

2. Description of Related Art

Celiac disease (CD) is a disease of the intestinal mucosa and is usually manifested in infants and children. CD is associated with an inflammation of the mucosa, which causes malabsorption. Individuals with celiac disease do not tolerate a protein called gluten, which is present in wheat, rye, barley and possibly oats. When exposed to gluten, the immune system of an individual with CD responds by attacking the lining of the small intestine. The only treatment of CD is a gluten-free diet, which usually results in morphological and clinical improvement.

Currently, the routine procedure to detect celiac disease is intestinal biopsy for checking damage to the intestinal lining. Recently, it has been reported that antibodies directed against gliadin, endomysial antigen (EMA), or reticulin can be detected in CD. Thus, ELISAs for gliadin and immunofluorescence assays for EMA and reticulin have been suggested for the diagnosis of CD. Further, since transglutaminase (tTG) has been identified as the endomysial antigen involved in CD, immunological assays are being proposed to detect antibodies using tTG as the antigen (Schuppan et al., WO 98/03892, 1998).

Gliadins are a class of proteins that can be isolated from wheat. These include the alpha, gamma, epsilon, delta and omega gliadins. Antibodies to gliadins have been reported in CD. Thus, immunoreactivity is observed against the gliadins as well as against glutenin, which is a partially purified fraction of wheat and contains gliadins.

Transglutaminases (EC 2.3.2.13) are a diverse family of $Ca^{2+}$ dependent enzymes that are highly ubiquitous and highly conserved across species. Transglutaminases catalyze the covalent cross-linking of specific proteins through the formation of isopeptide bonds between α-carboxyl groups of glutamine residues in one polypeptide and $\epsilon$-$NH_2$ groups of lysine residues in another. The resulting polymer network is stable and resistant or proteolysis, increasing the resistance of tissue to chemical, enzymatic and mechanical disruption. Of all the transglutaminases, tissue transglutaminases (tTG) is the most widely distributed. tTG provides the focus of the autoimmune response in CD, and has therefore been used for diagnosis of CD.

Although immunoassay techniques have been described for gladins and tTG for the diagnosis of CD, these assays do not detect all cases of celiac disease or sprue that are detected by intestinal biopsy. As a result, there is an ongoing need for the development of sensitive non-invasive tests for the diagnosis of celiac disease.

SUMMARY OF THE INVENTION

The present invention discloses a method for the diagnosis of celiac disease that is more sensitive that the methods of the prior art. The present method comprises detecting antibodies in the sera of patients to a combination of transglutaminase and its substrate such as gliadin, glutenin or other peptides having multiple glutamines. The sensitivity of the method detecting antibodies to a combination of tTG and its substrates is greater than the additive sensitivity of detecting antibodies to tTG alone or its substrates alone.

Accordingly, it is an object of the present invention to provide a sensitive method for the diagnosis of celiac disease.

It is another object of the present invention to provide a method of diagnosing celiac disease comprising the step of detecting the presence of antibodies to the combination of tTG and one or more substrates of tTG.

DESCRIPTION OF PREFERRED EMBODIMENTS

The term "substrate of tTG" or "tTG substrate" as used herein for the purposes of specification and claims means a peptide or polypeptide, irrespective of whether or not it is an enzymatic substrate of tTG, that interacts with tTG such that hidden epitopes on the substrate or tTG are exposed, the exposure of the hidden epitopes being detected as a synergistic increase in the detection of antibodies. An example of a substrate of tTg is a peptide or polypeptide having multiple glutamines such as polyglutamine, protamine sulfate or natural substrates such as gliadins and glutenin.

The present invention relates to increasing the sensitivity of diagnosis of celiac disease by detecting the presence of antibodies to tTG in the presence of its substrate. It was unexpectedly observed that when tTG was allowed to interact with a substrate prior to contact with the sample containing antibodies, the sensitivity of detection increased synergistically.

In one embodiment, the substrate of tTG was gliadin. That the increased sensitivity was not simply due to the detection of antibodies to tTG and to gliadin was demonstrated by the synergistic increase in the detection. Thus, more samples were detected as positive when tTG was allowed to react with its substrate (gliadin) prior to contact with the antibodies, than when either tTG alone or gliadin alone was used as the antigen. Further, when tTG was incubated with a substrate not known to be a natural substrate, i.e., protamine sulfate, a similar increase in sensitivity was observed. Although not intending to be bound by any particular theory, it is considered that tTG undergoes conformational change upon interacting with a substrate and in doing so, exposes epitopes that are relevant in vivo and that are not available without the substrate.

For the method of the present invention, the substrate of tTG is coated on to a solid matrix. Any standard immunoassay solid matrix such as a microtitre plate, beads and the like can be used. Transglutaminase (tTG) can be purified from any source such as murine, porcine, equine, human, monkey etc., or can be prepared by recombinant technology. tTG is also available commercially. Substrates for tTG are, or contain, peptides or polypeptides having multiple glutamine residues. Suitable substrates for tTG may be natural substrates such as gliadins or glutenin, or substrates not known to be natural substrates like protamine sulfate or polyglutamine. When the substrates of tTG is soluble only in an acidic medium, as is the case with gliadins and glutenin, it is preferable to coat a solid matrix first with the substrate in an acidic medium such as acetic acid. After a suitable period of coating, excess acid is washed away and then tTG is added. In the case of substrates that do not require an acidic medium for solubilization, such as protamine sulfate, substrate and tTg may be coated on a solid matrix in any order or the two may be incubated together in aqueous solution and then coated on to a solid matrix.

For example, in one embodiment, the solid matrix can be coated with gliadin, glutenin or both. In a preferred embodiment, the gliadin is gamma gliadin. Determination of appropriate concentrations of the substrate and tTG are well within the purview of one skilled in the art. In one embodiment, gliadin and glutenin were used in the range of 250 ng/ml to 3 µg/ml. Next, the solid matrix can be coated with tTG. In one embodiment, the concentration of tTG for coating was 5 ug/ml to 20 ug/ml. After removal of unbound antigens, nonspecific binding sites on the solid matrix can be blocked by methods well known in the art. The tTG plus substrate coated solid matrix can be used immediately for testing patient sera, or can be stored up to 2 years.

Antibodies associated with celiac diseases can be detected in patient sera using the solid matrix as coated above. Briefly, serum at a suitable dilution is incubated with the solid matrix coated with tTG and its substrate. Unbound materials are removed using standard techniques and bound antibodies are detected and quantitated using enzyme linked or fluorescent detection agents. These techniques are well known in the art of immunoassays. For example, for detection of antibodies of human origin, an anti-human IgG, IgM or IgA or antigen binding fragments thereof having a detectable label may be used. The detectable label may be an enzyme including, but not limited to, alkaline phosphatase, β-lactamase, β-galactosidase, urease or horseradish peroxidase. In a preferred embodiment, the label is alkaline phosphatase or horseradish peroxidase. Suitable substrates for these enzymes are well known in the art and include p-nitrophenyl-phosphate, 5-bromo-4-chloro-3-indolyl-phospate, 3,3-diaminobenzidine, and -phenylenediamine.

The presence of antibodies to tTG plus its substrate is considered to be an indication of the presence of CD.

The following examples are provided to illustrate the invention and are not intended to be restrictive.

EXAMPLE 1

This embodiment illustrates the coating of a solid matrix with the antigens (tTG plus substrates) and detection of specific antibodies using the antigen-coated solid matrix. In this illustration, prior to coating the plates with tTG, the microtitre plates are coated with glutenin and gliadin (γ-gliadin). Both glutenin and gliadin were dissolved in 1 mM acetic acid (57 µl glacial acetic acid in 1 L distilled water). at 2.5 µg/ml concentration and mixed to make a uniform solution. One hundred microliters of the glutenin-gamma gliadin mixture were added to each of the microtitre well. Plates were incubated at 2–8° C. overnight. Next, the plates were coated with 100 µl of tTG solution, prepared at a concentration of 10 µg/ml in a coating buffer (7.88 g of Tris-HCl, 8.7 g of NaCl, and 0.735 g of calcium chloride dihydrate in 1 L H$_2$O). The plates were incubated overnight at 2–8° C., washed four times with tTG wash buffer (7.88 g of Tris-HCl, 8.76 g of NaCl, 3.72 g of EDTA disodium salt, 1 mM Tween 20 in 1 L H$_2$O). The washed plates were incubated with blocking buffer (1% calf serum in PBS, 0.09% sodium azide). After blocking, the plates were washed with tTG wash buffer and dried. Patient serum was diluted 1:50 in serum diluent (1% calf serum in PBS) and 100 ul of the diluted patient serum was added to the plates and the plates were incubated for 1 hour at room temperature (RT). Unbound materials were removed by washing with PBS. Alkaline phosphatase conjugated anti-human IgA was added to the plates for about 30 minutes. Unbound materials were removed by washing. An alkaline phosphatase substrate was added to develop color, and detection and quantitation was performed using a spectrophotometer.

The results of an experiment, wherein detection of antibodies was carried out with plates coated with i) tTG, glutenin and gliadin, ii) only glutenin and gliadin, and iii) only tTG are presented below in Table 1.

TABLE 1

| Sera ID Col. A | tTG, gliadin and glutenin coated (EU/ml) Col. B | glutenin and gliadin coated (EU/ml) Col. C | tTG coated (EU/ml) Col. D | EMA titre Col. E |
|---|---|---|---|---|
| 98-5901 | 198.8* | 21.0* | 33.4* | 640* |
| 97-2043 | 28.7* | 5.4 | 9.7 | 160* |
| 97-4684 | 64.8* | 6.5 | 8.0 | 320* |
| 97-2873 | 63.4* | 6.5 | 25.4* | 160* |
| 97-6405 | 49.0* | 16.2* | 0.0 | 160* |
| 97-2449 | 35.4* | 2.2 | 0.0 | 320* |
| 98-1537 | 68.8* | 7.8 | 19.8 | 160* |

The cutoff value for each assay is 20EU/ml. Values that are above the cutoff value are positive and are indicated by an asterisk. Column A indicates the sera identity. Column E indicates that the sera selected for this analysis are all anti-endomysial antigen positive (Gold Standard diagnostic criteria) as determined by immunofluorescence assay. Column B shows the result of the values obtained by using the method of the present invention. As described above, this method includes pre-coating of the plates with glutenin and gamma gliadin followed by the addition of tTG. In contrast, when the same samples were tested using plates coated with tTG alone (column D) or with glutenin and gamma gliadin, without tTG (column C), most of the values were below the cutoff value and hence would be deemed negative. While not intending to be bound by any particular theory, it is considered that the conditions of column B, allows the tTG to interact with its substrate, gliadin and glutenin, thereby eliciting the Celiac Disease specific epitopes on tTG that can be efficiently recognized by the method of the present invention.

EXAMPLE 2

This embodiment demonstrates that increased sensitivity is achieved by using a single substrate of tTG. To illustrate this embodiment, the detection was carried out essentially as described in Example 1 for samples that were positive using a combination of glutenin and γ-gliadin. Briefly, microtitre plates were coated with α-gliadin, γ-gliadin or glutenin. After washing to remove unbound materials, the plates were incubated with tTG. After incubation, plates were washed and an aliquot of test samples was added to the wells. Color development was carried out by alkaline phosphatase labeled anti-human IgA followed by the addition of a substrate for alkaline phosphatase. Color was quantitated in a spectrophotometer. Samples with a reading of 3 Standard deviations above the control were marked as positive. The results from a representative sample are presented in Table 2.

TABLE 2

| Sample | α-gliadin | γ-gliadin | glutenin | γ-gliadin + glutenin |
|---|---|---|---|---|
| 98-6317 | positive | positive | positive | positive |
| 98-3810 | positive | positive | ND | positive |
| 98-840 | positive | positive | positive | positive |
| 98-6316 | positive | positive | positive | positive |
| 98-5798 | ND | positive | positive | positive |
| 97-2101 | positive | positive | positive | positive |
| 97-6719 | positive | positive | positive | positive |
| 97-49 | positive | ND | ND | positive |
| 97-1048 | positive | positive | positive | positive |

ND indicates not determined.

These results demonstrate that using a single substrate such as α- or γ-gliadin or the partially purified fraction glutenin, which contains gliadins, is equally effective for the method of the present invention.

EXAMPLE 3

This embodiment demonstrates that to increase sensitivity of the assay, tTG can be incubated with a natural substrate as described above or a substrate not known to be a natural substrate but which contains multiple glutamine residues such as protamine sulfate. or polyglutamine. To illustrate this embodiment, tTG was incubated with protamine sulfate essentially as described in Example 1. Briefly, microtiter plates were coated with 50 ug/ml solution of protamine sulfate for 2 hours at room temperature. Plates were washed with PBS and incubated with 1 ug/well tTG for 1 hour at room temperature. Plates were washed with tTG wash buffer, blocked with 0.1% Triton-x-100 in PBS, washed three times with tTG wash buffer. Serum samples from patients that were known to be positive from EMA titers were then added to the wells. After incubation for 1 hour at room temperature, plates were washed and alkaline phophatase conjugated anti-human IgA was added. Following incubation for 30 minutes are room temperature, the plates were washed and the substrate for alkaline phosphatase was added. Color was quantitated in a spectrophotometer. The results are presented in Table 3.

TABLE 3

| SAMPLE | tTG + protamine sulfate | tTG + glutenin + γ-gliadin |
|---|---|---|
| 00-3638 | positive | positive |
| 98-1002 | positive | positive |
| 98-5901 | positive | positive |
| 97-2873 | positive | positive |
| 97-1062 | positive | positive |
| 97-6405 | positive | positive |
| 97-3082 | positive | positive |

These results indicate that all samples that were positive using tTG plus glutenin and gliadin, were also found to be positive with tTG plus protamine sulfate. Thus, both natural substrates of tTG and other peptides or polypeptides containing multiple glutamine residues can be used for the method of the present invention.

In a variation of this illustration, plates were coated with protamine sulfate, and then blocked with blocking buffer containing 0.1% triton x-100 in PBS prior to being coated with tTG and the plates were washed with tTG wash buffer. Detection was carried out as above. No difference was observed between blocking first and then incubating with tTG and incubating with tTG and then blocking.

These data indicate that the increased sensitivity observed in the present invention is achieved by allowing tTG to interact with its natural or unnatural substrates. While not intending to be bound by any particular theory, it is considered that tTG interacting with its substrate more accurately represents the situation in vivo and therefore, the sensitivity of the assay is closer to the sensitivity of the immunofluorescence detection techniques for the presence of EMA immunoreactivity in intestinal biopsied sections. Increasing the sensitivity of detection will help in the diagnosis of celiac disease without the necessity of a biopsy.

From the foregoing, it will be obvious to those skilled in the art that various modifications in the above-described methods, and compositions can be made without departing from the spirit and scope of the invention. Accordingly, the invention may be embodied in other specific forms without departing from the spirit or essential characteristics thereof. Present examples and embodiments, therefore, are to be considered in all respects as illustrative and not restrictive, and all changes which come within the meaning and range of equivalency of the specifications are therefore intended to be embraced therein.

What is claimed is:

1. A method for diagnosis of celiac disease in an individual comprising the steps of:
    (a) contacting transglutaminase with glutenin to form complexes of transglutaminase and glutenin;
    (b) contacting a sample of serum obtained from the individual with the complexes of transglutaminase and glutenin; and
    (c) detecting antibodies to the complexes of transglutaminase and glutenin in the sample from the individual,
    wherein the presence of the antibodies to the complexes of transglutaminase and glutenin is indicative of celiac disease and wherein the sensitivity of diagnosis of celiac disease is higher with detection of antibodies to the complexes of transglutaminase and glutenin than with detection of antibodies to transglutaminase alone or glutenin alone.

2. A method for diagnosis of celiac disease in an individual comprising the steps of:
    (a) contacting transglutaminase with a substrate mixture comprising glutenin and gliadin to form complexes of transglutaminase and the substrate mixture;
    (b) contacting a sample of serum obtained from the individual with the complexes of transglutaminase and the substrate mixture from (a); and
    (c) detecting antibodies to the complexes of transglutaminase and the substrate mixture in the serum sample from the individual,
    wherein the presence of the antibodies to the complexes of transglutaminase and the substrate mixture is indicative of celiac disease and wherein the sensitivity of diagnosis of celiac disease is higher with detection of antibodies to the complexes of transglutaminase and the substrate mixture than with detection of antibodies to transglutaminase alone or the substrate mixture alone.

3. A method for diagnosis of celiac disease in an individual comprising the steps of:
    (a) contacting transglutaminase with protamine sulfate to form complexes of transglutaminase and protamine sulfate;
    (b) contacting a sample of serum obtained from the individual with the complexes of transglutaminase and protamine sulfate; and (c) detecting antibodies to the complexes of transglutaminase and protamine sulfate in the sample from the individual, wherein the presence of the antibodies to the complexes of transglutaminase and protamine sulfate is indicative of celiac disease and wherein the sensitivity of diagnosis of celiac disease is higher with detection of antibodies to the complexes of transglutaminase and protamine sulfate than with detection of antibodies to transglutaminase alone or protamine sulfate alone.

4. The method of claim 2, wherein the gliadin is selected from the group consisting of α-gliadin and γ-gliadin.

5. The method of claim 4, wherein the gliadin is γ-gliadin.

6. A method for the detection of antibodies to a combination of transglutaminase and glutenin in a sample of serum obtained from an individual comprising the steps of:

(a) immobilizing glutenin on a solid matrix;

(b) incubating transglutaminase with the immobilized glutenin to form immobilized transglutaminase-glutenin complexes;

(c) contacting the serum sample with the immobilized transglutaminase-glutenin complexes to form immobilized antibody-transglutaminase-glutenin complexes;

(d) contacting the immobilized antibody-transglutaminase-glutenin complexes with a labeled affinity molecule to form labeled immobilized antibody-transglutaminase-glutenin complexes, wherein the labeled affinity molecule has a specific affinity for the antibodies;

(e) removing unimmobilized labeled molecules; and (f) detecting the presence of antibodies in the sample from the amount of immobilized labeled antibody complexes.

7. A method for the detection of antibodies to complexes of transglutaminase and a substrate mixture comprising glutenin and gliadin in a sample of serum obtained from an individual comprising the steps of:

(a) immobilizing the substrate mixture on a solid matrix;

(b) incubating transglutaminase with the immobilized substrate mixture to form immobilized transglutaminase-substrate mixture complexes;

(c) contacting the serum sample with the immobilized transglutaminase-substrate mixture complexes to form immobilized antibody-transglutaminase-substrate mixture complexes;

(d) contacting the immobilized antibody-transglutaminase-substrate mixture complexes with a labeled affinity molecule to form labeled immobilized antibody-transglutaminase-substrate mixture complexes, wherein the labeled affinity molecule has a specific affinity for the antibodies;

(e) removing unimmobilized labeled molecules; and (f) detecting the presence of antibodies in the sample from the amount of immobilized labeled antibody complexes.

8. A method for the detection of antibodies to a combination of transglutaminase and protamine sulfate in a sample of serum obtained from an individual comprising the steps of:

(a) immobilizing protamine sulfate on a solid matrix;

(b) incubating transglutaminase with the immobilized protamine sulfate to form immobilized transglutaminase-protamine sulfate complexes;

(c) contacting the serum sample with the immobilized transglutaminase-protamine sulfate complexes to form immobilized antibody-transglutaminase-protamine sulfate complexes;

(d) contacting the immobilized antibody-transglutaminase-protamine sulfate complexes with a labeled affinity molecule to form labeled immobilized antibody-transglutaminase-protamine sulfate complexes, wherein the labeled affinity molecule has a specific affinity for the antibodies;

(e) removing unimmobilized labeled molecules; and (f) detecting the presence of antibodies in the sample from the amount of immobilized labeled antibody complexes.

9. The method of claim 7, wherein the gliadin is selected from the group consisting of α-gliadin and γ-gliadin.

10. The method of claim 9, wherein the gliadin is γ-gliadin.

11. The method of claim 5, wherein the labeled affinity molecule is selected from the group consisting of anti-human IgG, IgA, IgM and antigenic binding fragments thereof.

12. The method of claim 11, wherein the label on the affinity molecule is selected from the group consisting of alakaline phosphatase, horseradish peroxidase, β-lactamase, β-galactosidase and urease.

* * * * *